United States Patent [19]

Horita et al.

[11] 4,371,726
[45] Feb. 1, 1983

[54] COMPOSITION SUITABLE FOR MECHANICAL POWER TRANSMISSION AND PROCESS FOR OPERATING TRACTION DRIVES

[75] Inventors: Yoshiharu Horita, Tokyo; Kenichi Fujimoto, Kanda; Michio Hoshino, Yokohama; Tetsuo Takito, Kawasaki; Masayoshi Muraki, Yokohama, all of Japan

[73] Assignees: Nippon Steel Chemical Co., Ltd.; Mitsubishi Oil Co., Ltd., both of Tokyo, Japan

[21] Appl. No.: 283,967

[22] Filed: Jul. 16, 1981

[30] Foreign Application Priority Data

Feb. 13, 1981 [JP] Japan ............................ 56/18990
Feb. 13, 1981 [JP] Japan ............................ 56/18991

[51] Int. Cl.³ .................. C10M 1/16; C10M 1/20
[52] U.S. Cl. .................................. 585/3; 585/2; 252/32.7 E; 252/52 R
[58] Field of Search ............. 585/3, 10; 252/32.7 E, 252/52

[56] References Cited

U.S. PATENT DOCUMENTS 3,411,369 11/1968 Hammann et al. ............... 585/10
3,440,894 4/1969 Hammann et al. ............... 74/200
3,925,217 12/1975 Green et al. ..................... 585/2

*Primary Examiner*—Jacqueline V. Howard
*Attorney, Agent, or Firm*—Gordon W. Hueschen

[57] ABSTRACT

The disclosure relates to a composition suitable for use in mechanical power transmission devices. It has as its principal component a hydrocarbon oil which has from 19 to 30 carbon atoms, inclusive, and three six-membered carbocyclic rings and consists of a mixture of compounds having the following formula:

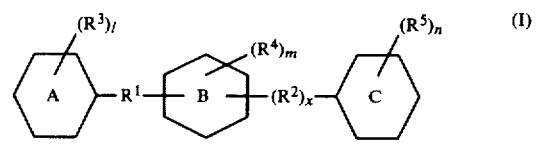

wherein $R^1$ is a divalent straight or branched chain radical $C_yH_{2y}$ where y is an integer of 1 through 3; $R^2$ is a straight chain radical $C_zH_{2z}$ where z is an integer of 1 through 3; $R^3$, $R^4$, and $R^5$ are the same or different alkyl groups having from 1 through 4 carbon atoms; l, m, and n each is an integer from zero through 3; and x is zero or 1; and wherein rings A and B are hydrogenated benzene rings and ring C is a hydrogenated benzene ring when x is 1 and a hydrogenated benzene ring or a cyclohexane ring when x is zero said hydrogenated benzene rings being saturated with hydrogen to the extent of at least 80% but less than 100% of the theoretical, and the composition can additionally contain one or more of an antioxidant, a rustproofing agent, a viscosity index improver, and antifoaming agent.

21 Claims, No Drawings

COMPOSITION SUITABLE FOR MECHANICAL POWER TRANSMISSION AND PROCESS FOR OPERATING TRACTION DRIVES

BACKGROUND OF THE INVENTION

1. Field of the Invention

This invention relates to a composition suitable for use in mechanical power transmission units. More particularly, the invention relates to compositions specifically adapted for use with traction drives and to a process for operating traction drives.

2. Prior Art

Heretofore, gears and hydraulic devices have been used for power transmission or speed control. A system of drives, called traction drives (rolling friction drive devices), which resort to point contact or line contact between rolling solid bodies has found recognition. These traction drives are particularly useful in industrial machines because they provide high power transmission efficiency without the vibration characteristic of devices using gears and like positive forms of engagement.

As the fluid to be interposed between contact parts of such traction drives, there must be selected a lubricant which proves most suitable from the functional point of view. Specifically, the fluid intervening between contact parts is required to possess an ability to undergo reversible glass transition, viscosity increasing, and enhance the efficiency of power transmission between surfaces of rolling contact under high pressure and, on departure from such contact surfaces, immediately return to its original fluid state. It must also be capable of precluding direct contact between metal bodies, preventing metal bodies from seizure, wear and fatigue damage and, similarly to lubricants of all kinds fulfilling important functions of preventing occurrence of rust and elevation of temperature.

Friction or traction drive devices for transmission of mechanical power have been disclosed in a number of reports in prior technical literature. They are dealt with in full detail in U.S. Pat. Nos. 3,394,603 and 3,411,369; the *Journal of Chemical and Engineering Data*, Vol. 5, No. 4, p.p. 499–507 (1960), and Hewko et al., in *Proceedings of the Symposium on Rolling Contact Phenomena*, p.p. 157–185 (1962), Elsevier, Amsterdam, Netherlands, for example.

As compositions for use in traction drives, a host of substances have been advanced, including mineral oils (Japanese Patent Publication No. 24,635/1964), mixtures of dialkyl aromatic hydrocarbons with diarylalkanes (Japanese Patent Publication 40,525/1972), polymethylmethacrylate (Japanese Pat. Publication No. 31,828/1973), adamantanes (Japanese Pat. Publications 42,067/1973 and 42,068/1973), polyolefins (Japanese Patents KOKAI 4,766/1971 and 2,229/1972) and alkylnaphthalenes (U.S. Pat. No. 2,549,377), for example. Japanese Patent KOKAI 40,726/1980 has proposed fluids which are obtained by hydrogenating bis-(α-methylbenzyltoluene) and/or bis-(α-methylbenzyl)-xylene.

Besides, proposals abound which concern naphthenic oils having naphthenic rings. These naphthenic oils include dicyclohexylethane (U.S. Pat. No. 3,577,361), dicyclohexylpropane (Japanese Patent Publication 36,105/1978), hydrogenated condensation ring compounds (U.S. Pat. No. 3,411,369), naphthenes containing at least one saturated carbon-containing cyclic ring (U.S. Patent 3,440,894), naphthenes containing at least two saturated carbon-containing cyclic rings (U.S. Pat. Nos. 3,925,217), and mixtures of naphthenes and paraffins (U.S. Pat. Nos. 3,595,796 and 3,595,797), and an oil which is obtained by hydrogenating the product of alkylation of xylene and/or toluene with styrene (Japanese Patent KOKAI No. 43,108/1980), for example.

U.S. Pat. Nos. 3,440,894 and 3,925,217 mentioned above embrace a wide range of naphthenic compounds and cite a large number of naphthenes by way of example. Most of them are compounds which possess one or two hydrogenated rings. Among the compounds disclosed therein, those which possess three or more hydrogenated rings are limited to a small number, including tercyclohexyls 1,2,3-tricyclohexylpropane and tricyclohexylmethane, for example. Although they have a high traction factor, they have poor practical use because of high viscosity or high crystal-precipitating temperature. It is noted from the prior technical literature that naphthenic oils containing hydrogenated rings are possessed of generally outstanding properties for lubricants, particularly those to be used in traction drives.

OBJECTS OF THE INVENTION

An object of this invention, therefore, is to provide novel compositions suitable for use in mechanical power transmission devices. Another object of the invention is to provide such compositions which excel in traction properties and other properties such as resistance to oxidation and resistance to corrosion and which are easily synthesized from inexpensive raw materials on a commercial scale. Still another object is to provide a novel process for operating traction drives. Other objects are to avoid the disadvantages of the prior art and to obtain such advantages as will appear as the description proceeds.

SUMMARY OF THE INVENTION

The objects described above are accomplished by provision of a composition suitable for use in mechanical power transmission units, consisting essentially of a minor amount of an antioxidant in admixture with a hydrocarbon oil which has from 19 through 30 carbon atoms and three six-membered carbocyclic rings and consists of a mixture of compounds having the following formula:

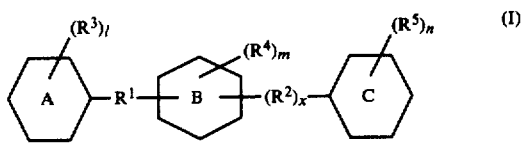

wherein $R^1$ is a divalent straight or branched chain radical $C_yH_{2y}$ where y is an integer of 1 through 3; $R^2$ is a straight chain radical $C_zH_{2z}$ where z is an integer of 1 through 3; $R^3$, $R^4$, and $R^5$ are the same or different alkyl groups having from 1 through 4 carbon atoms; l, m, and n each is an integer from zero through 3; and x is zero or 1; and wherein rings A and B are hydrogenated benzene rings and ring C is a hydrogenated benzene ring when x is 1 and a hydrogenated benzene ring or a cyclohexane ring when x is zero, said hydrogenated benzene rings being saturated with hydrogen to the extent of at least 80% but less than 100% of the theoretical and said hydrocarbon oil being otherwise unsaturated. Advantageously, the rings are saturated to at least 95%.

In one form of the invention it is preferred that x in the formula is 1; in another, that it is zero. Preferred compounds in such cases include hydrogenated 1-(benzylphenyl)-1-phenylethane having from zero to two, inclusive, methyl substituents and from zero to two, inclusive, ethyl substituents; hydrogenated dibenzylbenzene having from zero to two, inclusive, methyl substituents and from zero to two, inclusive, ethyl substituents; hydrogenated benzylbiphenyl having from zero to two, inclusive, methyl substituents and from zero to two, inclusive, ethyl substituents; and, hydrogenated 1-biphenyl-1-phenylethane having from zero to two, inclusive, methyl substituents and from zero to two, inclusive, ethyl substituents.

Advantageously, the composition contains additionally up to 100 parts, preferably 10 to 60 parts, of an alkylcyclohexane in which the alkyl group contains from 9 through 20 carbon atoms for each 100 parts of said hydrocarbons.

The invention also relates to a process for operating traction drives which have an area of point or line contact between rolling solid bodies in which the area of contact is oiled with the above composition.

Thus, it has been found that a mixture of hydrocarbons having a backbone wherein three hydrogenated benzene rings are linearly linked through the medium of two chains, $C_yH_{2y}$ and $C_zH_{2z}$, or two hydrogenated benzene rings are linearly linked directly by a $C_yH_{2y}$ group and a hydrogenated benzene or cyclohexane ring is linked to one of them without any intervening chain, because of its peculiar molecular structure, is specifically effective in fulfilling the objects of the present invention.

DETAILED DESCRIPTION OF THE INVENTION

The principal component of the hydrocarbon oil of this invention for use in mechanical power transmission devices is a naphthenic-type hydrocarbon compound having 19 to 30 carbon atoms, inclusive, and three hydrocarbon benzene rings and is represented by the aforementioned general formula I, wherein y and z in $R^1$ and $R^2$ severally are 1, 2, or 3, preferably y is 1 or 2 and z 1, $R^3$, $R^4$, and $R^5$ severally are alkyl groups having 1 to 4 carbon atoms, inclusive, preferably 1 or 2 carbon atoms, l, m, and n severally are zero, 1, 2, 3, or desirably, zero, 1, 2, or 3 and preferably, zero, 1 or 2, and x is either zero or 1.

Where x is 1, therefore, the compound of the general formula I can be expressed by the general formula II. Where x is zero, therefore, this compound can be expressed by the general formula III.

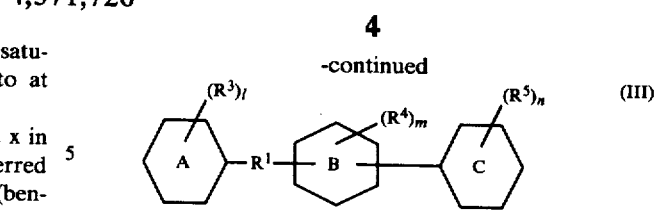

wherein $R^1$, $R^2$, $R^3$, $R^4$, $R^5$, l, m and n have the same meanings as defined above and ring C in formula III is a hydrogenated benzene or a cyclohexane ring.

Where x is 1, the compounds represented by the general formula I include hydrogenated dibenzylbenzenes, hydrogenated (methylbenzyl)-benzylbenzenes, hydrogenated (dimethylbenzyl)-benzylbenzenes, hydrogenated di-(methylbenzyl)benzenes, hydrogenated (ethylbenzyl)-benzylbenzenes, hydrogenated di-(ethylbenzyl)-benzenes, hydrogenated (diethylbenzyl)-benzylbenzenes, hydrogenated dibenzyltoluenes, hydrogenated dibenzyl-dimethylbenzenes, hydrogenated dibenzyl-ethylbenzenes, hydrogenated (methylbenzyl)-benzyltoluenes, hydrogenated (dimethylbenzyl)-benzyltoluenes, hydrogenated (ethylbenzyl)-benzyltoluenes, hydrogenated di-(methylbenzyl)toluenes, hydrogenated di-(ethylbenzyl)toluenes, hydrogenated di-(methylbenzyl)xylenes, hydrogenated 1,1-(benzylphenyl)-phenylethanes, hydrogenated 1,1-[(methylbenzyl)-phenyl]-phenylethanes, hydrogenated 1,1-(benzylphenyl) (methylphenyl)-ethanes, hydrogenated 1,1-(benzylmethylphenyl)-phenylethanes, hydrogenated 1,1-(benzylphenyl) (ethylphenyl)ethanes, hydrogenated 1,1-(benzylethylphenyl)-phenylethanes, hydrogenated phenethylbenzylbenzenes, hydrogenated phenethyl-benzyltoluenes, hydrogenated diphenethylbenzenes, and hydrogenated diphenethyl-toluenes, for example.

Among the compounds represented by the general formula II mentioned above, hydrogenated dibenzylbenzenes and hydrogenated (benzylphenyl)-phenylethanes or the derivatives thereof incorporating one to two methyl or ethyl substituents, particularly hydrogenated dibenzyltoluenes, are especially suitable for the objects of the present invention.

Where x is 0, the compounds represented by the general formula I mentioned above include hydrogenated benzylbiphenyls, hydrogenated benzyl-monomethylbiphenyls, hydrogenated benzyldimethyl-biphenyls, hydrogenated benzyl-trimethyl-biphenyls, hydrogenated benzyl-monoethyl-biphenyls, hydrogenated benzyl-diethyl-biphenyls, hydrogenated benzyl-triethyl-biphenyls, hydrogenated biphenylyltolyl-methanes, hydrogenated (methyl-bi-phenylyl)tolyl-methanes, hydrogenated (dimethylbiphenylyl)tolyl-methanes, hydrogenated (trimethylbiphenylyl)tolyl-methanes, (ethylbiphenylyl)tolyl-methanes, hydrogenated (diethylbiphenylyl)tolyl-methanes, hydrogenated (biphenylyl) (ethylphenyl)-ethanes, hydrogenated (methylbiphenylyl) (ethylphenyl)-methanes, hydrogenated (dimethylbiphenylyl) (ethylphenyl)-methanes, hydrogenated (trimethylbiphenylyl) (ethylphenyl)-methanes, hydrogenated (ethylbiphenylyl) (ethylphenyl)-methanes, hydrogenated (diethylbiphenylyl) (ethylphenyl)-methanes, hydrogenated 1-biphenylyl-1-phenylethanes, hydrogenated 1-(methylbiphenylyl)-1-phenylethanes, hydrogenated 1-(dimethylbiphenylyl)-1-phenylethanes, hydrogenated 1-(ethylbiphenylyl)-1-phenylethanes, hydrogenated 1-(diethylbiphenylyl)-1-phenylethanes, hydrogenated 1-biphenylyl-1-(methylphenyl)ethanes, hydrogenated 1-(ethylbiphenylyl)-1-(methyl-

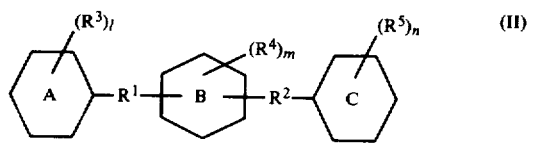

phenyl)ethanes, hydrogenated 1-(methylbiphenylyl)-1-(methylphenyl)ethanes, hydrogenated 1-biphenylyl-1-(ethylphenyl)ethanes, hydrogenated 1-(methylbiphenylyl)-1-(ethylphenyl)ethanes, hydrogenated 1-(dimethylbiphenylyl)-1-(ethylphenyl)ethanes, hydrogenated 1-(ethylbiphenylyl)-1-(ethylphenyl)ethanes, hydrogenated phenethylbiphenyls, hydrogenated phenethyl-methylbiphenyls, hydrogenated phenethyl-dimethylbiphenyls, hydrogenated phenethyl-ethylbiphenyls, hydrogenated phenethyl-diethylbiphenyls, hydrogenated (methylphenethyl)biphenyls, hydrogenated (methylphenethyl)-methylbiphenyls, hydrogenated (methylphenethyl)-ethylbiphenyls, and hydrogenated (ethylphenethyl)biphenyls, for example.

Among the compounds which are represented by the general formula III mentioned above, hydrogenated benzylbiphenyls or derivatives thereof incorporating one or two methyl or ethyl substituents are particularly suitable for the objects of this invention.

The compound of the general formula II such as, for example, hydrogenated dibenzylbenzenes are obtained by hydrogenating dibenzylbenzene resulting from the reaction of benzyl halides and benzene in the presence of a Friedel-Crafts catalyst. Among other benzyl halides, benzyl chloride proves advantageously useful. Advantageously, the benzyl halides are used in an amount of not more than 1 mol, preferably in the range of from 0.1 to 0.5 mol per mol of benzene. Among other compounds usable as Friedel-Crafts catalysts, sulfuric acid, boron trifluoride and aluminum chloride prove particularly suitable, with aluminum chloride as the best choice. The amount of aluminum chloride to be used is desired to fall in the range of from 0.0001 to 0.1 mol, per mol of benzyl chloride. Although the reaction temperature can be selected in the range of from 20° to 150° C., it is preferably chosen from the range of from 40° to 80° C. Although the reaction pressure has only to exceed the minimum level required for maintaining the contents of the reactor in a liquid phase, the pressure in the range of from 0 to 10 kg/cm$^2$G proves advantageous for the sake of the reaction. This reaction affords as its product dibenzylbenzene which is a mixture of ortho, meta and para isomers. These isomers may be subjected to hydrogenation in their mixed form or in their separated form. Preparatory to the hydrogenation, the Friedel-Crafts catalyst is removed from the reaction mixture as by washing with water and the unreacted portions of reactants and possibly by-products of reaction are expelled from the reaction mixture as by distillation to isolate dibenzylbenzene. Then, the isolated reaction product is treated in the presence of a hydrogenation catalyst to undergo hydrogenation.

As the hydrogenation catalyst, a platinum, palladium, rhodium, ruthenium or nickel catalyst functions advantageously. The nickel catalyst is used in an amount within the range of from 0.1 to 20 weight percent. The hydrogen pressure is suitable in the range of from 10 to 200 kg/cm$^2$G. The hydrogen for the hydrogenation is used in an amount of 9 mols or more per mol of dibenzylbenzene, preferably 1.1 times the mol ratio mentioned above. The reaction temperature of hydrogenation is in the range of from 100° to 200° C., preferably from 140° to 170° C. When the hydrogenation has proceeded to a predetermined ratio of hydrogenation, the reaction is stopped and followed by isolation of hydrogenated dibenzylbenzene. This isolation of the reaction product may be obtained by simply removing the used catalyst. It may be effected by separation through filtration or optionally by any of ordinary methods adopted for treatment of lubricants such as, for example, treatment with activated clay. When necessary, distillation may be adopted for this purpose. Little advantage, however, is usually derived from the distillation unless the reaction has produced low boiling compounds as by-products because, by distillation, separation of fully hydrogenated dibenzylbenzene and partially hydrogenated dibenzylbenzene or separation of isomers is obtained only with great difficulty.

Production of an alkyl-substituted hydrogenated dibenzylbenzene is accomplished by substituting benzene or benzyl halides or both respectively with an alkyl-substituted benzene or alkyl-substituted benzyl halides or both as the raw materials and using these raw materials in suitable combinations. Suitable alkyl-substituted benzenes for this purpose are toluene, ethylbenzene, propylbenzene, xylene, cumene, diethylbenzene, and methylethylbenzene. Suitable alkyl-substituted benzyl halides for the purpose include derivatives of benzyl halides incorporating monomethyl or monoethyl substituents. When such alkyl-substituted raw materials are adopted, the reaction can be carried out under similar conditions as described above and the hydrogenation can be performed similarly.

When a compound represented by the general formula:

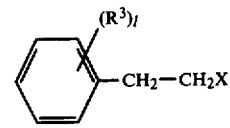

(wherein, R$^3$ and l have the same meanings as defined above and X stands for a halogen) is used in the place of the aforementioned benzyl halides or an alkyl-substituted derivative thereof, there can be obtained hydrogenated diphenethyl benzene or an alkyl-substituted derivative thereof.

In a preferred embodiment of the method for the manufacture of the compounds of this invention, a hydrogenated (benzylphenyl)-phenyl alkane-type compound is obtained by reacting a diphenyl alkane with benzyl halides in the presence of a Friedel-Crafts catalyst to afford a (benzylphenyl)-phenyl alkane and subsequently hydrogenating this reaction product. In this case, when a 1,1-diphenyl alkane is used as the diphenyl alkane, there is produced a hydrogenated 1-(benzylphenyl)-1-phenyl alkane-type compound. Use of an alkyl-substituted 1,1-diphenyl alkane or an alkyl-substituted benzyl halide or both results in production of a hydrogenated alkyl-substituted 1-(benzylphenyl)-1-phenyl alkane-type compound. When a 1,3-diphenyl alkane is used as the diphenyl alkane, there is obtained a hydrogenated 1-(benzylphenyl)-3-phenyl alkane-type compound and when a 1,2-diphenyl alkane is used, there is obtained a 1-benzylphenyl-2-phenyl alkane or a 2-benzylphenyl-1-phenyl alkane. In all these cases, the kind of the Friedel-Crafts catalyst, the conditions of the Friedel-Crafts reaction of alkyl halides, the conditions of the hydrogenation, etc., are similar to those described above. The aforementioned 1,1-diphenyl alkanes can be obtained by the reaction of ethylbenzene or styrene and benzene in the presence of the Friedel-Crafts catalyst.

The compounds of the general formula III such as, for example, hydrogenated benzylbiphenyl are obtained, similarly to those of the general formula II, by hydrogenating benzylbiphenyls resulting from the reaction of benzyl halides with biphenyls in the presence of the Friedel-Crafts catalyst. In this case, the amount of aluminum chloride to be used is desired to fall in the range of from 0.0001 to 0.05 mol per mol of benzyl chloride. Although the reaction temperature can be selected in the range from a level exceeding the melting point of the biphenyls involved to 180° C., it is preferably selected in the range of from 70° to 100° C. Although the reaction pressure has only to exceed the minimum level required for maintaining the contents of the reactor in a liquid phase, it is preferred to fall in the range of from 0 to 50 kg/cm²G. This reaction affords as its product benzylbiphenyl, which is a mixture of ortho, meta and para isomers. These isomers may be subjected to hydrogenation either in their mixed form or in their separated form. Preparatory to the hydrogenation, the reaction mixture is washed with water and distilled to effect removal of the unreacted reactants and the used Friedel-Crafts catalyst and isolation of benzylbiphenyl. The isolated benzylbiphenyl is then hydrogenated by introduction of hydrogen in the presence of a hydrogenation catalyst. In this case, the conditions for the hydrogenation are the same as those adopted in the hydrogenation for the production of the compounds of general formula II.

Production of a hydrogenated alkyl-substituted benzylbiphenyl is accomplished by substituting a biphenyl or a benzyl halide or both respectively with an alkyl-substituted biphenyl or an alkyl-substituted benzyl halide or both as the raw materials by using these raw materials in suitable combinations. Suitable alkyl-substituted biphenyls are monomethylbiphenyl, monoethylbiphenyl, monopropylbiphenyl, dimethylbiphenyl, diethylbiphenyl, and methylethylbiphenyl. And suitable alkyl-substituted benzyl halides are derivatives of benzyl halides incorporating monomethyl, monoethyl and other similar substituents. When these alkyl-substituted derivatives are used, the reaction can be carried out under similar conditions, as described above. The hydrogenation can also be performed similarly.

When a compound represented by the general formula:

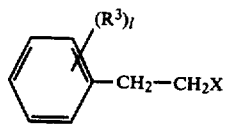

(wherein $R^3$ and $l$ have the same meanings as defined above and X stands for a halogen) is used in the place of the aforementioned benzyl halides or an alkyl-substituted derivative thereof, there can be obtained hydrogenated phenethylbiphenyl or an alkyl-substituted derivative thereof.

Another preferred embodiment of the method for the manufacture of the compound of this invention comprises the steps of reacting cyclohexylbenzene or a biphenyl with styrene in the presence of the Friedel-Crafts catalyst and hydrogenating the resultant reaction product. Suitable Friedel-Crafts catalysts for this reaction are boron trifluoride, aluminum chloride and sulfuric acid. When sulfuric acid is adopted as the catalyst, the amount of this catalyst is desired to fall in the range of from 5 to 50 weight percent based on the amount of the biphenyl involved. The cyclohexylbenzene or biphenyl and styrene are preferably used in equal or nearly equal mol proportions in order to preclude the otherwise possible polymerization of styrene in the reaction. The reaction temperature is desired to be low, falling on the order of from 0° to 30° C. When the reaction is terminated, the reaction mixture is washed with water to effect removal of the used catalyst and then distilled to effect isolation of 1-(biphenylyl)-1-phenylethane or 1-(cyclohexylphenyl)-1-phenylethane as the reaction product.

The compound, when subjected to hydrogenation by the same method as described above, produces hydrogenated 1-(biphenylyl)-1-phenylethane.

When a similar procedure is repeated by using an alkyl-substituted cyclohexylbenzene or an alkyl-substituted biphenyl or an alkyl-substituted styrene respectively in the place of cyclohexylbenzene or biphenyl or styrene, there is obtained an alkyl-substituted hydrogenated 1,-(biphenylyl)-1-phenylethane. Alkyl-substituted cyclohexyl benzenes suitably usable for the purpose are cyclohexylmethylbenzenes, cyclohexyl-ethylbenzenes, cyclohexyl-propylbenzenes, cyclohexyl-dimethylbenzenes, cyclohexyl-diethylbenzenes, (methylcyclohexyl)benzenes, (dimethylcyclohexyl)benzenes, (ethylcyclohexyl)benzenes, (diethyl-cyclohexyl)benzenes, and mixtures thereof. Alkyl substituted biphenyls suitably useful herein are the same as those cited above. Suitable alkyl-substituted styrenes include those compounds represented by the general formula:

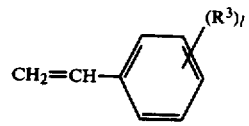

(wherein $R^3$ and $l$ have the same meanings). A typical example of these compounds is vinyl toluene. Also, α-methylstyrene can be used similarly with advantage. When these alkyl-substituted derivatives are utilized, the reaction can be carried out under similar conditions as described above.

The composition of the present invention for use in mechanical power transmission devices can be used in its independent form. When it is mixed with an alkyl(-$C_9$-$C_{20}$) cyclohexane added thereto in an amount of at most 100 parts by weight, preferably in the range of from 10 to 60 parts by weight, based on 100 parts by weight of the compound of this invention, there can be obtained a composition possessed of a varying degree of viscosity useful in mechanical power transmission devices without substantially degrading the properties which the oil is expected to possess to fulfill its function. Alkyl cyclohexanes suitable for this purpose are obtained by hydrogenating alkylbenzenes derived by the reaction of trimer through pentamer of propylene with benzene.

The compositions of the invention can contain, in addition to its essential ingredients, namely, a minor amount of an antioxidant and a hydrocarbon oil as above described, can contain other additives or by-products as long as they do not detract from its suitability for use in mechanical power transmission. Thus, in addition to antioxidants, the compositions can contain such additives as rustproofing agents, antifoam agents, and the like. They also can include a small amount of the by-products which occur in the course of the production of the hydrocarbon oils represented by the general formula I. However, a large amount of aromatic hydrocarbons or compounds possessing a double bond are desirably avoided. In the production of a compound represented by the general formula I by the hydrogenation of a corresponding aromatic hydrocarbon, therefore, the hydrogenation is desired to be performed until the hydrogenation reaches at least 80% of completion, desirably 95% and preferably more than 95%. Substantially complete hydrogenation, e.g., removal to less than 1% is practically impossible. Such complete removal of unsaturation, however, is not called for, because the objects of this invention are not obstructed by the presence of unsaturated compounds in small amounts. Thus, the hydrocarbon oils which constitute the essential components of the compositions of the invention are mixtures of components in different stages of hydrogenation or isomers or both and can be used as such or in combination with suitable additives, as mentioned above.

The reference to hydrogenated compounds, accordingly, is to be understood to include such compounds which have been hydrogenated to at least 80%, preferably to at least 95%, of the theoretical.

The traction coefficient of a given oil is generally measured by use of a traction drive device. In the present invention, the measurement has been made by use of a Soda's four roller machine friction tester. (T. Kimura and M. Muraki "TRIBOLOGY", 1979 (12), p. 255). In this tester, traction (rolling friction) occurs at the three areas of contact formed between an inner centrally located roller and three outer rollers tangentially located around the inner central roller. These rollers are arranged so that equal perpendicular loads are caused to bear on the three areas of contact. The surface pressure of contact as expressed by the average Hertzian pressure falls in the range of from 0.575 to 1.157 GPa. The other conditions for the determination of traction by this tester are as shown in Table 1 below.

TABLE 1

| Conditions for determination of traction | | |
|---|---|---|
| Speed of rotation | 1.05 to 4.19 m/sec | |
| Speed of sliding | 0 to 0.22 m/sec | |
| Test rollers | Material | bearing steel, SUJ-2 |
| | Hardness (Hv) | 760 to 800 |
| | Dimensions | 40mm × 9mm (outer rollers) |
| | (diam × width) | 40mm × 5mm (central roller) |
| Method of lubrication - Dripping about 10 ml/min in flow volume | | |
| Feed oil temperature | | 28° C. |

The procedure of the test comprised first setting the central and outer rollers rotating at a fixed speed, applying a load to bear upon these rollers and thereafter accelerating the rotational speeds of the outer rollers while keeping that of the central roller constant thereby inducing slide/roll ratios to permit continuous measurements of the change in the friction torque or the traction coefficient. The friction torque was determined by directly measuring the torsional moment of the centerlessly-supported shaft of the central roller with a resistance-wire strain meter.

The traction coefficient determined under the conditions mentioned above tends first to rise in a straight line with the increasing slide/roll ratios, then reach a peak and start falling. Of the curve thus drawn, the important zone from the standpoint of the practical use of oil falls in the first portion of straight line in which the magnitude of heat generated by the shearing of the oil film is not large. Thus, the traction coefficient specifically within this zone will be considered exclusively herein below.

Under the test conditions of 1.157 GPa of average Hertzian pressure and 4.19 m/s of rotational speed, for example, the following traction coefficients were obtained.

| | viscosity (cst) at 40° C. | traction coefficient |
|---|---|---|
| Naphthenic mineral oil | 8.0 | 0.050 |
| Hydrogenated Polyisobutylene | 10.0 | 0.060 |
| Dicyclohexane | 2.9 | 0.065 |
| Ethyl Dicyclohexane | 4.0 | 0.060 |
| Methylcyclohexyl Cyclohexylmethane | 4.2 | 0.065 |
| Dicyclohexylethane | 4.0 | 0.070 |
| sec-Dodecylcyclohexane | 5.4 | 0.050 |
| Tercyclohexyls (o- and m-mixture)* | 30 | 0.090 |
| Hydrogenated α-Methylstyrene linear dimer | 22 | 0.090 |

*crystal was precipitated at room temperature.

In contrast, the traction coefficient of the compound obtained by the present invention reached as high as 0.095, a value definitely higher than the values found for the aforementioned hydrocarbons. It has been found consequently that the product of this invention even excels hydrogenated α-methylstyrene linear dimer, which is now marketed as a 'best' synthetic traction fluid.

In addition to traction coefficient and oxidation stability, the composition for mechanical power transmission is required to have a pour point or freezing point of at least −10° C. and is preferred to have a viscosity at 40° C. under atmospheric pressure of 7—150 cst.

| | viscosity (cst) at 40° C. | pour point or freezing point (°C.) |
|---|---|---|
| o-tercyclohexyl | — | 45 |
| m-tercyclohexyl | — | 63 |
| p-tercyclohexyl | — | 162 |
| m-, p-tercyclohexyls mixture | 30 | crystal was precipitated at room temperature |
| tricyclohexymethane | — | 59 |
| 1,1,3-tricyclohexyl propane | about 2500 | — |

As being clear from above, the above-mentioned compounds are not appropriate as a base oil for the composition for mechanical power transmission.

Further, in order to secure stable operation of a traction device for a long time, the composition for mechanical power transmission is required to have good sealing properties. Following table shows the sealing properties of the composition for mechanical power transmission using base oils having appropriate viscosity as the composition and relatively good traction property. The tests were carried out at 120° C. for 70 hours on nitrile rubber (Buna N) and acrylic rubber based on a method of JIS K-6301.

| Property | Base oil | | | |
|---|---|---|---|---|
| | Examples 1 & 4 | | Hydrogenated α-methylstyrene linear dimer oil | |
| | Rubber | | | |
| | Nitrile rubber (Buna N) | Acrylic rubber | Nitrile rubber (Buna N) | Acrylic rubber |
| Increase of weight (%) | 3.45 | 1.48 | 7.30 | 3.86 |
| Increase of volume (%) | 6.58 | 3.42 | 13.6 | 7.67 |
| Tensile strength (Kgf/cm²) | 195 | 81 | 168 | 85 |
| Elongation (%) | 260 | 140 | 150 | 110 |
| Variation of hardness (%) | −6 | 0 | −6 | −1 |
| Aniline point | 85° C. | | 70° C. | |

The oil in accordance with the present invention can be used in itself, but addition of the additives is a preferable embodiment.

In addition to the traction characteristics described above, the oil for use in traction drives needs to possess properties usually expected of ordinary lubricants such as, for example, oxidation stability, resistance to the corrosive action of a viscosity index improver, resistance to wear, rustproofness, rubber swelling property, and ability to prevent foaming. Thus, depending on the nature of use, suitable additives, for example, 2,6-di-tertiary-butyl-para-cresol and other similar alkyl phenols, zinc dialkyl-dithiophosphate and other similar sulfur-phosphorous compounds can be incorporated as antioxidants; amines, esters and metal salts as rustproofing agents; polymethacrylates as viscosity index improvers; and siliconetype polymers as antifoaming agents, can be included.

Now, the present invention will be described more specifically below with reference to working examples. Wherever "parts" or "percentages" are mentioned in the following examples, and elsewhere herein, they are by weight unless otherwise specified.

In the following examples, a composition suitable for use in traction drives was prepared by adding to the hydrogenated dibenzyltoluene, or like oil, according to the invention, 2,6-di-tertiary-butyl-para-cresol and zinc dialkyl-dithiophosphate as antioxidants, each in the amount of 0.5 weight percent. This oil was tested for traction coefficient under the aforementioned conditions and then subjected to an oxidation test by the procedure described in Paragraph 3.2 (Testing Method for Oxidation Stability of Internal Combustion Engine Oil of Japanese Industrial Standard (JIS) K-2514-1980 (Testing Method for Oxidation Stability of Lubricating Oils).

EXAMPLE 1

To 3 parts of toluene was added 0.002 to 0.01 part of aluminum chloride. The mixture was heated to 70° C. and then allowed to react with 1 part of benzyl chloride added thereto for two hours. The reaction mixture was washed with water to remove the used catalyst and then distilled to expel the unreacted portion of reactants. The dibenzyltoluene (mixture of isomers) thus obtained was supplied to an autoclave and, in the presence of a nickel catalyst, subjected to hydrogenation for four hours under the conditions of 40 kg/cm²G of initial hydrogen pressure and 200° C. of temperature, to afford hydrogenated dibenzyltoluene (mixture of isomers). The general attributes of this hydrogenated dibenzyltoluene were as shown in Table 2. The results of the oxidation test were as shown in Table 3. For the purpose of comparison, a commercially available hydrogenated α-methylstyrene linear dimer-type oil for traction drives and an oil prepared from a naphthenic mineral oil were subjected to the same tests.

The oxidation test was carried out under the following conditions.

| Amount of test specimen | 300 ml |
|---|---|
| Temperature | 165.5° C. |
| Time | 72 hours |
| Oxidation catalyst | Copper and iron |

EXAMPLE 2

To 4 mols of 1,1-diphenylethane was added 0.001 to 0.005 mol of aluminum chloride. The mixture was heated to 60° C. and allowed to react upon 1 mol of benzyl chloride added thereto for 20 minutes. Then, the reaction mixture was washed with water to remove the used catalyst and subsequently distilled to expel the unreacted portions of the reactants. The isolated 1-(benzylphenyl-1-phenylethane (mixture of isomers) was supplied to an autoclave and, in the presence of a nickel catalyst, subjected to hydrogenation under the conditions of 100 kg/cm²G of initial hydrogen pressure, 140° to 170° C. of temperature for five hours, to afford hydrogenated 1-(benzylphenyl)-1-phenylethane (mixture of isomers). The general attributes of this reaction product were as shown in Table 2.

This product, compounded as above, was tested for traction coefficient and subjected to the oxidation test, as specified in Paragraph 3.2 of JIS K-2514-1980. The results were shown in Table 3.

EXAMPLE 3

A hydrogenated monoethyl-substituted 1-(benzylphenyl)-1-phenylethane, a mixture of compounds of the formulas

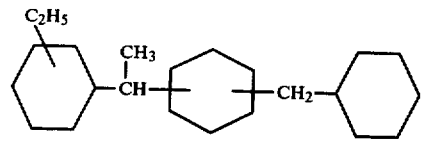

and

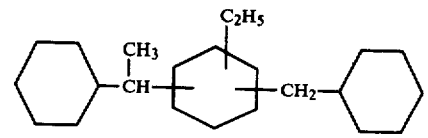

was obtained by following the procedure of Example 2, except that 4 mols of monoethyl-substituted 1,1-diphenylethane was used in the place of 1,1-diphenylethane. The general attributes of this reaction product were as shown in Table 2. This product, compounded as above, was tested for traction coefficient and subjected to the oxidation test specified in Paragraph 3.2 of JIS K-2514-1980. The results were as shown in Table 3.

TABLE 2

| | General Attributes | | |
|---|---|---|---|
| Property | Hydrogenated dibenzyl toluene | Hydrogenated 1-(benzyl-phenyl)-1-phenylethane | Hydrogenated monoethyl-substituted 1-(benzyl-phenyl)-1-phenylethane |
| Specific gravity (15/4° C.) | 0.90 | 0.90 | 0.89 |
| Appearance | Colorless, clear | Colorless, clear | Colorless, clear |
| Viscosity (cst) (40° C.) | 66 | 106.5 | 616.5 |
| Viscosity (cst) (100° C.) | 5.8 | 7.6 | 14.5 |
| Pour point (°C.) | −20 | −20 max. | −20 max. |
| Flash point (°C.) | 152 | — | — |
| Hydrogenation ratio (%) | 99 | 98 | 98 |

TABLE 3

| | Traction Coefficient and Result of Oxidation Test | | | | |
|---|---|---|---|---|---|
| Item of test | Example 1 | Example 2 | Example 3 | Hydrogenated α-Methyl-styrene linear dimer oil for traction drives | Naphthenic oil |
| Traction coefficient | 0.094 | 0.09 | 0.09 | 0.09 | 0.05 |
| Oxidation Test: Viscosity ratio* | 1.08 | 1.10 | 1.08 | 1.20 | 8.24 |
| Increase of total acid number (mg KOH/g) | 0.06 | 0.10 | 0.08 | 0.40 | 3.7 |
| Heptane insolubles after oxidation test (weight %) | 0.12 | 0.15 | 0.18 | 0.28 | 5.72 |

*Viscosity after oxidation test/initial viscosity

EXAMPLE 4

To 5 parts of biphenyl was added 0.001 to 0.005 part of aluminum chloride. The mixture was heated to 70° C. and then allowed to react upon 1 part of benzyl chloride added thereto for 20 minutes. The reaction mixture was washed with water to remove the used catalyst and then distilled to expel the unreacted fractions of the reactants. The produced benzylbiphenyl (a mixture of isomers) was supplied to an autoclave having an inner volume of 1 liter and, in the presence of a nickel catalyst, subjected to hydrogenation under the conditions of 100 kg/cm²G of initial hydrogen pressure and 140° to 170° C. temperature for two hours, to afford hydrogenated benzylbiphenyl (a mixture of isomers). The general attributes of this hydrogenated benzylbiphenyl were as shown in Table 4.

This product, compounded as described above with 0.5 weight percent each of 2,6-di-tertiary-butyl-para-cresol and zinc dialkyl-dithiophosphate as antioxidants, was tested for traction coefficient and subjected to the oxidation test as specified in Paragraph 3.2 of JIS K-2514-1980. The results were as shown in Table 5.

EXAMPLE 5

A hydrogenated benzyl-monoethylbiphenyl, a mixture of compounds of the formulas

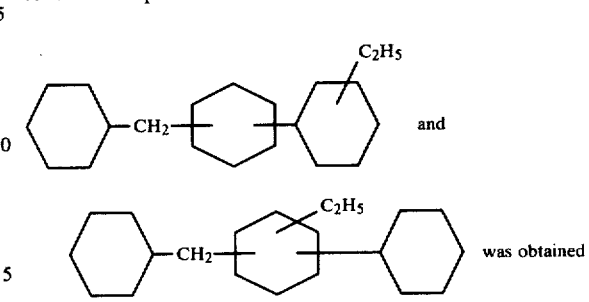

was obtained by following the procedure of Example 4, except 5 parts of monoethylbiphenyl and 0.03 part of aluminum chloride were used. The general attributes of this reaction product were as shown in Table 4. This product, compounded as described above, was tested for traction coefficient and subjected to the oxidation test specified in Paragraph 3.2 of JIS K-2514-1980. The results were as shown in Table 5.

EXAMPLE 6

In a reactor, 1 liter or cyclohexylbenzene and 200 ml of concentrated sulfuric acid were introduced and the resultant mixture was kept at 15° C. Then, 800 ml of a 1:1 mixture of cyclohexylbenzene and styrene was added dropwise to the resultant mixture over a period of two hours, while the temperature of the mixture was kept in the range of from 15° to 20° C. At the end of the dropwise addition of the mixture, 200 ml of concentrated sulfuric acid was added to continue the reaction further for 30 minutes. Then, the reaction mixture was washed repeatedly with water to remove residual sulfuric acid and then distilled to isolate 1-(cyclohexylphenyl)-1-phenylethane (a mixture of structural isomers). Then, 1 liter of 1-(cyclohexylphenyl)-1-phenylethane was introduced in the autoclave and, in the presence of a nickel catalyst, subjected to hydrogenation under the conditions of 100 kg/cm²G of initial hydrogen pressure and 140° to 170° C. temperature for two hours, to afford hydrogenated 1-(biphenylyl)-1-phenylethane (a mixture of structural isomers). The general attributes of this hydrogenation product were as shown in Table 4.

A composition suitable for traction drives prepared by incorporating into this hydrogenation product the same additives as given above, was tested for traction coefficient and subjected to the oxidation test specified in Paragraph 3.2 of JIS K-2514-1980. The results were as shown in Table 5.

EXAMPLE 7

Hydrogenated 1-(ethylbiphenylyl)-1-phenylethane, a mixture of compounds of the formulas

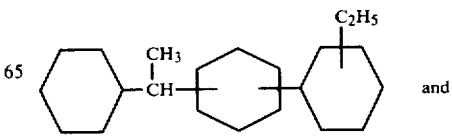

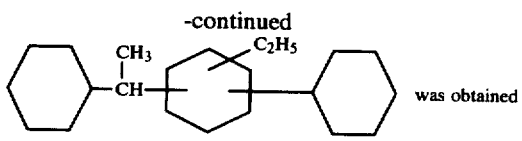

was obtained was obtained by following the procedure of Example 6, except 1 liter of monoethylbiphenyl was used in the place of cyclohexylbenzene and 800 ml of a 1:1 mixture of monoethylbiphenyl and styrene was used in the place of the mixture of cyclohexylbenzene and styrene. The general attributes of this product were shown in Table 4. This product, compounded as given above, was tested for traction coefficient and then subjected to the oxidation test specified in Paragraph 3.2 of JIS K-2514-1980. The results were as shown in Table 5.

TABLE 4

General Attributes

| Property | Hydrogenated benzylbiphenyl | Hydrogenated benzylmonoethyl biphenyl | Hydrogenated 1-(biphenylyl)-1-phenyl-ethane | Hydrogenated 1-(ethylbiphenylyl)-1-phenyl-ethane |
|---|---|---|---|---|
| Specific gravity (15/4° C.) | 0.95 | 0.93 | 0.93 | 0.93 |
| Appearance | Colorless, clear | Colorless, clear | Colorless, clear | Colorless, clear |
| Viscosity (cst)(40° C.) | 41.2 | 68.9 | 80.2 | 201 |
| Viscosity (cst)(100° C.) | 4.9 | 6.5 | 7.0 | 10.5 |
| Pour point (°C.) | −15 | −20 max. | −20 max. | −17.5 max. |
| Hydrogenation ratio (%) | 98 | 98 | 98 | 98 |

TABLE 5

Traction Coefficient and Result of Oxidation Test

| Item of Test | Example 4 | Example 5 | Example 6 | Example 7 | Hydrogenated α-Methyl-styrene linear dimer oil for traction drives | Naphthenic oil |
|---|---|---|---|---|---|---|
| Traction coefficient | 0.095 | 0.09 | 0.09 | 0.09 | 0.09 | 0.05 |
| Oxidation Test: Viscosity ratio | 1.06 | 1.10 | 1.08 | 1.08 | 1.20 | 8.24 |
| Increase of total acid number (mg KOH/g) | 0.06 | 0.08 | 0.08 | 0.06 | 0.40 | 3.7 |
| Heptane insolubles after oxidation test (weight %) | 0.15 | 0.20 | 0.18 | 0.15 | 0.28 | 5.72 |

EXAMPLE 8

Dodecylbenzene obtained by the reaction of propylene tetramer with benzene was introduced into an autoclave and, in the presence of a nickel catalyst, subjected to hydrogenation under the conditions of 50 kg/cm²G of initial hydrogen pressure and 150° C. of temperature for 4 hours, to afford alkylcyclohexane. An oil for traction drives was prepared by mixing 50 parts by volume of this alkylcyclohexane with 50 parts by volume of the hydrogenated dibenzyltoluene obtained in Example 1 and incorporating into this mixture 0.5 weight percent, based on the amount of the mixture, each of 2,6-di-tertiarybutyl-para-cresol and zinc dialkyl-dithiophosphate. This fluid was tested for traction coefficient and subjected to the oxidation test as specified in Paragraph 3.2 of JIS K 2514-1980. The results of the tests are shown together with the general attributes in Table 6.

EXAMPLE 9

By following the procedure of Example 8, an oil for traction drives was prepared from 50 parts by volume of alkylcyclohexane obtained in Example 8 and 50 parts by volume of hydrogenated benzylbiphenyl obtained in Example 4. Then, the fluid was subjected to the same tests as described in Example 8. The results were as shown in Table 6.

TABLE 6

| General Attributes | | |
|---|---|---|
| Property | Example 8 | Example 9 |
| Specific gravity (15/4° C.) | 0.88 | 0.87 |
| Appearance | Colorless, clear | Colorless, clear |
| Viscosity (cst)(40° C.) | 20.2 | 17.5 |
| Viscosity (cst)(100° C.) | 3.4 | 3.1 |
| Pour point (°C.) | −37.5 | −35 |
| Flash point (°C.) | 150 | 150 |
| Hydrogenation ratio (%) | 98 | 98 |

| Traction Coefficient and Result of Oxidation Test | | |
|---|---|---|
| Item of Test | Example 8 | Example 9 |
| Traction coefficient | 0.086 | 0.088 |
| Oxidation Test: | | |
| Viscosity ratio | 1.08 | 1.07 |
| Increase of total acid number (mg KOH/g) | 0.07 | 0.05 |
| Heptane insolubles after oxidation text (weight %) | 0.15 | 0.13 |

As shown by the Examples, the addition of dodecylcyclohexane gave compositions having substantially lower viscosities and substantially lower pour points without substantial loss in traction coefficient or stability to oxidation.

It is to be understood that the invention is not to be limited to the exact details of operation or exact compounds, compositions, methods, or procedures shown and described, as obvious modifications and equivalents will be apparent to one skilled in the art.

We claim:

1. A composition, suitable for use in mechanical power transmission units, consisting essentially of a minor amount of an antioxidant in admixture with a hydrocarbon oil which has from 19 through 30 carbon atoms and three six-membered carbocyclic rings and consists of a mixture of compounds having the following formula:

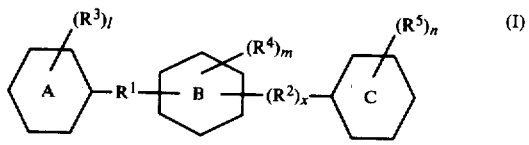

wherein $R^1$ is a divalent straight or branched chain radical $C_yH_{2y}$ where y is an integer of 1 through 3; $R^2$ is a straight chain radical $C_zH_{2z}$ where z is an integer of 1 through 3; $R^3$, $R^4$, and $R^5$ are the same or different alkyl groups having from 1 through 4 carbon atoms; l, m, and n each is an integer from zero through 3; and x is zero or 1; and wherein rings A and B are hydrogenated benzene rings and ring C is a hydrogenated benzene ring when x is 1 and a hydrogenated benzene ring or a cyclohexane ring when x is zero said hydrogenated benzene rings being saturated with hydrogen to the extent of at least 80% but less than 100% of the theoretical and said hydrocarbon oil being otherwise unsaturated.

2. A composition according to claim 1, in which said benzene rings are saturated to at least 95%.

3. A composition according to claim 1, in which x in the formula is 1.

4. A composition according to claim 3, in which said hydrocarbon comprises hydrogenated 1-(benzylphenyl)-1-phenylethane having from zero to two, inclusive, methyl substituents and from zero to two, inclusive, ethyl substituents.

5. A composition according to claim 3, in which said hydrocarbon comprises hydrogenated dibenzylbenzene having from zero to two, inclusive, methyl substituents and from zero to two, inclusive, ethyl substituents.

6. A composition according to claim 5, in which x in the formula is zero.

7. A composition according to claim 6, in which said hydrocarbon comprises hydrogenated benzylbiphenyl having from zero to two, inclusive, methyl substituents and from zero to two, inclusive, ethyl substituents.

8. A composition according to claim 6, in which said hydrocarbon comprises hydrogenated 1-biphenyl-1-phenylethane having from zero to two, inclusive, methyl substituents and from zero to two, inclusive, ethyl substituents.

9. A composition according to claim 1, which contains additionally up to 100 parts of an alkylcyclohexane in which the alkyl group contains from 9 through 20 carbon atoms for each 100 parts of said hydrocarbons.

10. A composition according to claim 9, which contains additionally from 10 to 60 parts of an alkylcyclohexane in which the alkyl group contains from 9 through 20 carbon atoms for each 100 parts of said hydrocarbons.

11. A process for operating traction drives which have an area of point or line contact between rolling solid bodies which comprises oiling the area of contact with hydrocarbon oil which has from 19 through 30 carbon atoms and three six-membered carbocyclic rings and consists of a mixture of compounds having the following formula:

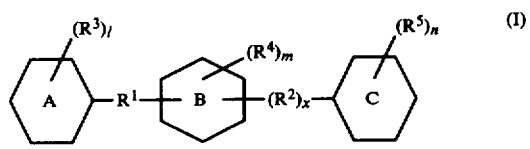

wherein $R^1$ is a divalent straight or branched chain radical $C_yH_{2y}$ where y is an integer of 1 through 3; $R^2$ is a straight chain radical $C_zH_{2z}$ where z is an integer of 1 through 3; $R^3$, $R^4$, and $R^5$ are the same or different alkyl groups having from 1 through 4 carbon atoms; l, m, and n each is an integer from zero through 3; and x is zero or 1; and wherein rings A and B are hydrogenated benzene rings and ring C is a hydrogenated benzene ring when x is 1 and a hydrogenated benzene ring or a cyclohexane ring when x is zero said hydrogenated benzene rings being saturated with hydrogen to the extent of at least 80% but less than 100% of the theoretical and said hydrocarbon oil being otherwise unsaturated.

12. A process of claim 11, in which the rings are saturated to at least 95%.

13. A process of claim 11, in which the hydrocarbon oil is stabilized by an antioxidant.

14. A process according to claim 11, in which x in the formula is 1.

15. A process of claim 11, in which said hydrocarbon comprises hydrogenated (benzylphenyl)-phenylethane having from zero to to two, inclusive, methyl substituents and from zero to two, inclusive, ethyl substituents.

16. A process of claim 11, in which said hydrocarbon comprises hydrogenated dibenzylbenzene having from zero to two, inclusive, methyl substituents and from zero to two, inclusive, ethyl substituents.

17. A process of claim 11, in which x in the formula is zero.

18. A process of claim 11, in which said hydrocarbon comprises hydrogenated benzylbiphenyl having from zero to two, inclusive, methyl substituents and from zero to two, inclusive, ethyl substituents.

19. A process of claim 11, in which said hydrocarbon comprises hydrogenated biphenyl-phenylethane having from zero to two, inclusive, methyl substituents and from zero to two, inclusive, ethyl substituents.

20. A process of claim 11, which contains additionally up to 100 parts of an alkylcyclohexane in which the alkyl group contains from 9 through 20 carbon atoms for every 100 parts of said hydrocarbons.

21. A process of claim 11, which contains additionally from 10 to 60 of an alkylcyclohexane in which the alkyl group contains from 9 through 20 carbon atoms for every 100 parts of said hydrocarbons.

* * * * *